United States Patent [19]

Fried

[11] Patent Number: 5,336,811

[45] Date of Patent: Aug. 9, 1994

[54] PROCESS FOR THE PREPARATION OF ALDEHYDES

[75] Inventor: Herbert E. Fried, Houston, Tex.

[73] Assignee: Shell Oil Company, Houston, Tex.

[21] Appl. No.: 108,361

[22] Filed: Aug. 18, 1993

[51] Int. Cl.$^5$ .............................................. C07C 45/00
[52] U.S. Cl. .................................... 568/436; 568/426
[58] Field of Search ...................... 568/426, 431, 436

[56] References Cited

U.S. PATENT DOCUMENTS

| | | | |
|---|---|---|---|
| 4,620,033 | 10/1986 | Isshiki et al. | 562/519 |
| 5,136,101 | 8/1992 | Fried | 568/402 |
| 5,136,102 | 8/1992 | Fried | 568/402 |
| 5,136,103 | 8/1992 | Fried | 568/402 |
| 5,155,278 | 10/1992 | Fried | 568/471 |
| 5,155,279 | 10/1992 | Fried | 568/471 |
| 5,162,579 | 11/1992 | Fried | 562/537 |
| 5,166,422 | 11/1992 | Fried | 562/537 |
| 5,166,423 | 11/1992 | Fried | 562/537 |
| 5,175,359 | 12/1992 | Fried | 562/537 |
| 5,175,360 | 12/1992 | Fried | 562/538 |
| 5,179,218 | 1/1993 | Fried | 554/134 |

FOREIGN PATENT DOCUMENTS

50-96516 7/1975 Japan .

OTHER PUBLICATIONS

Miyaza et al., "Oxodation of Benzyl Alcohol with Iron (III) Using Polymers Containing Nitroxyl Radical Structure as a Mediator," J. Polym. Sci. Polym. Chem. Ed., 23(9), 1985, pp. 2487–2494.
Grigor'ev et al., "Participation of Nitroxyl Radical in the Oxidation of Aldehyde and Alcohol Groups in 3-imidazolin-1-oxyls," Izc. Akad. Nauk SSSR, Ser. Khim., (1), 1978, pp. 208–210.
Miyazawa et al., "Oxidation of Benzyl Alcohol with Copper(II) Mediated by a Polymeric Oxoaminium Salt," J. Mol. Catal., 49(1), 1988, 131–134.
Ganem et al., "Biological Spin Labels as Organic Reagents. Oxidation of Alcohols to Carbonyl Compounds Using Nitroxyls," J. Org. Chem., 40(13), 1975, pp. 1998–2000.
Miyazawa et al., "Oxidation of Benzyl Alcohol by Iron-(III) Mediated by Nitroxyl Radical." J. Mol. Catal., 31(2), 1985, pp. 217–220.
Annelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org.
Inokuchi et al., "A Selective and Efficient Method for Alcohol Oxidations Mediated by N-Oxoammonium Salts in Combination with Sodium Bromite," J. Org. Chem., 1990, 55 pp. 462–466.
Organic Synthesis, vol. 69, p. 212 (1990).
Semmelhack et al., "Oxidation of Alcohols to Aldehydes with Oxygen and Cupric Ion, Mediated by Nitrosonium Ion," J. Am. Chem. Soc. 1984, 106, 3374–3376.
Yamaguchi et al., "Application of Redox System Based on Nitroxides to Organic Synthesis," Pure & Applied Chemistry, vol. 62(2), 1990, 217–222.
E. R. Kagan et al., "Chemistry of Hindered Amines from the Piperidine Series", Synthesis, pp. 895–916.
R. M. Dupeyre et al., "Nitroxides. XIX. Norpseudopelletierine-N-oxyl, a New, Stable, Unhindered Free Radical", pp. 3180–3181.
E. R. Rozantsev et al., "Synthesis and Reaction of Stable Nitroxyl Radicals I. Synthesis" Synthesis, Apr. 1971, pp. 190–202.
E. R. Rozantsev et al., "Synthesis and Reaction of Stable Nitroxyl Radicals II. Reactions," Synthesis, Apr. 1971, pp. 401–414.

*Primary Examiner*—Werren B. Lone
*Attorney, Agent, or Firm*—Pamela J. McCollough

[57] ABSTRACT

A process for the preparation of an aldehyde by reacting the corresponding aryl methanol with a stable free radical nitroxide in the presence of a $NO_x$-generating compound at a temperature in the range of from about 0° C. to about 100° C. and thereafter separating out the aldehyde.

25 Claims, No Drawings

PROCESS FOR THE PREPARATION OF ALDEHYDES

FIELD OF THE INVENTION

This invention relates to a process for the preparation of aldehydes by the oxidation of the corresponding aryl methanols in the presence of a stable free radical nitroxide and a $NO_x$-generating compound.

BACKGROUND OF THE INVENTION

It is known to use nitroxyl radicals/oxoammonium salts in the oxidation of primary alcohols to produce aldehydes and acids and secondary alcohols to ketones (*Journal of Organic Chemistry*, vol. 52 (12), pp. 2559–2562, and *Journal of Organic Chemistry*, vol. 55, 1990, pp. 462–466).

It is reported in the open literature that primary aliphatic alcohols can be converted to aldehydes in 30–40% yields in the presence of catalytic amounts of cuprous chloride, 2,2,6,6,-tetramethylpiperidine-1-oxyl, and atmospheric oxygen (*Journal of American Chemical Society*, 1984, 106, pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217–222).

It has been found that aldehydes can be produced in good yields and with high selectivities from aryl methanols without producing large amounts of other products such as acids and esters. This can be accomplished by using catalytic amounts of a stable free radical nitroxide, a $NO_x$-generating compound and optionally, an oxidant and/or a solvent.

SUMMARY OF THE INVENTION

This invention relates to a process for the preparation of an aldehyde which comprises reacting the corresponding aryl methanol with a stable free radical nitroxide having the formula:

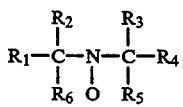

wherein
(1) (a) each of $R_1$, $R_2$, $R_3$ and $R_4$ is an alkyl, aryl or substituted alkyl group having 1 to about 15 carbon atoms, and (b) $R_5$ and $R_6$ (i) each is an alkyl group having 1 to about 15 carbon atoms provided that $R_1$–$R_6$, are not all alkyl groups, or a substituted alkyl group having 1 to about 15 carbon atoms wherein the substituent is hydrogen, cyano, —$CONH_2$, —$OCOCH$, $OCOC_2H_5$, carbonyl, alkenyl wherein the double bond is not conjugated with the nitroxide moiety, or —COOR wherein R of the —COOR group is alkyl or aryl, or (ii) together form part of a ring that contains at least 3 carbon atoms and up to two heteroatoms of O or N, or
(2) the

moiety and the

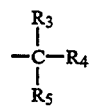

moiety individually are aryl, or
(3) the

moiety and the

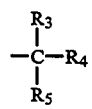

moiety together form a bicyclic ring with the proviso that the group directly adjacent to the N—O moiety is a bridgehead C—H, or a fully alkylated carbon, in the presence of a $NO_x$-generating compound and optionally, a solvent and/or an oxidant, at a temperature in the range of from about 0° C. to about 100° C. and thereafter separating out the aldehyde.

DESCRIPTION OF THE PREFERRED EMBODIMENTS

The present process converts aryl methanol s to the corresponding aldehydes by contacting the aryl methanol with a stable free radical nitroxide in the presence of a $NO_x$-generating compound, a solvent and an oxidant at a temperature in the range of from about 0° C. to about 100° C. and thereafter separating out the aldehyde.

The aryl methanol reactant suitably comprises one or more aryl methanol s, i.e., Ar—$CH_2OH$, having a carbon number in the range of from about 5 to about 50, preferably from about 6 to about 30, and more preferably from about 6 to about 20. Aryl methanols typically suitable for use in the present invention include benzyl alcohol, naphthyl alcohol, anthracenyl alcohol, furfuryl alcohol and the like. It is contemplated that these aryl methanols may have any number of substituents which do not interfere with the oxidation of the hydroxy group. Suitable substituents include sulfonyl, nitro, chloro, carbamoyl and the like.

The process of the instant invention is particularly suited to aryl methanols with about 6 to about 30, preferably about 6 to about 20 carbon atoms. In a preferred embodiment, the aryl methanol reactant i s selected from the group consisting of benzyl alcohol, 4-nitrobenzyl alcohol, 3-chlorobenzyl alcohol, 4-methylbenzyl alcohol, 4-chlorobenzyl alcohol, 3-methylbenzyl alcohol, 3-ethylbenzyl alcohol, 3-methoxybenzyl alcohol and mixtures thereof, with benzyl alcohol being particularly preferred.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of aryl methanols to the corresponding aldehydes. These catalysts are generated in situ by the oxidation of a stable free radical nitroxide to an oxoammonium salt with an oxygen-containing oxidant. The stable free radical nitroxide can be obtained by the oxidation of amines or hydroxyl amines.

The stable free radical nitroxides which are suitable for use in the instant invention have the formula:

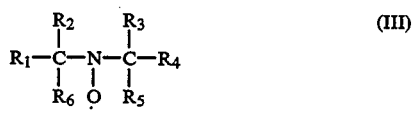
(III)

wherein each of $R_1$, $R_2$, $R_3$ and $R_4$ is an alkyl, aryl or substituted alkyl groups and no hydrogen is bound to the remaining valences on the carbon atoms bound to the nitrogen. As used herein, the term "alkyl" is meant to include cycloalkyl. The alkyl (or substituted) groups $R_1$-$R_4$ may be the same or different, and preferably contain 1 to 15 carbon atoms. Preferably, $R_1$-$R_4$ are methyl, ethyl, or propyl groups. In addition to hydrogen, the substituents may include, halogen, oxygen, nitrogen and the like.

The remaining valences ($R_5$ and $R_6$) in formula III above may be satisfied by any atom or group except hydrogen which can bond covalently to carbon, although some groups may reduce the stabilizing power of the nitroxide and are undesirable. When $R_1$, $R_2$, $R_3$ and $R_4$ are each alkyl groups, however, at least one of $R_5$ and $R_6$ must be an aryl group. Preferably, $R_5$ and $R_6$ are substituted alkyl groups having 1 to about 15 carbon atoms wherein the substituent is selected from halogen, cyano, —COOR, wherein R is alkyl or aryl, —CONH$_2$, —OCOC$_2$H$_5$, carbonyl, or alkenyl where the double bond is not conjugated with the nitroxide moiety, or alkyl groups of 1 to about 15 carbon atoms.

The remaining valences ($R_5$ and $R_6$) in formula III above may also form a ring containing at least three carbon atoms and up to two heteroatoms, such as O or N. $R_5$ and $R_6$ can, for example, form a five-membered ring containing 3 carbon atoms and up to two heteroatoms, such as O or N, a five-membered ring containing 4 carbon atoms, a six-membered ring containing 5 carbon atoms, a seven-membered ring containing 6 carbon atoms, an eight-membered ring containing 7 carbon atoms, etc. For purposes of this invention, it is preferred that $R_5$ and $R_6$ together form a five-membered ring, a six-membered ring, a seven-membered ring, or an eight-membered ring, although larger rings would also be suitable. Examples of suitable compounds having the structure above and in which $R_5$ and $R_6$ form part of the ring are 2,2,6,6,-tetramethylpiperidine-1-oxyl, 2,2,5,5-tetramethylpyrrolidin-1-oxyl, 2,2,7,7-tetramethylcycloheptan-1-oxyl, mixtures thereof, and the like. It is understood that these compounds may contain substituents which do not interfere with the reaction.

The

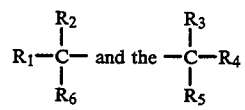

moieties in formula III above can individually be aryl, i.e.,

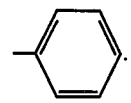

Examples of suitable compounds having the structure above in which the

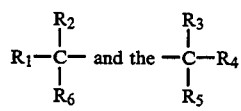

moieties are individually aryl are diphenylamine-n-oxyl, phenol tertiary butylamine-N-oxyl, 3-methyldiphenylamine-N-oxyl, 2-chlorophenylamine-N-oxyl and the like. These compounds may be substituted with an substituents which do not interfere with the reaction.

The

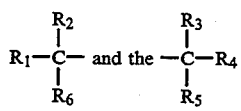

moieties in formula III above can also form a bicyclic ring wherein the group adjacent to the N—Ȯ moiety is either a bridgehead C-H or a quaternary carbon. As used herein, the term "bridgehead C—H" refers to a tertiary carbon which is common to both rings of the bicyclic ring system. As used herein, "a quarternary carbon" refers to a fully substituted carbon atom having alkyl, aryl or substituted alkyl groups having 1 to about 18 carbon atoms as substituents. Examples of suitable compounds having the structure above in which the

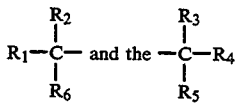

moieties form a bicyclic ring are 2-azabicyclo[2.2.1]heptan-2-oxyl, 2-azabicyclo[2.2.2]-3,3-dimethyloctan-2-oxyl, 3azabicyclo[3.2.2]-2,2,4,4-tetramethylnonan-3-oxyl and the like. These compounds may be substituted with any substituents which do not interfere with the reaction.

In a preferred embodiment, the stable free radical nitroxide is a piperidine-1-oxyl having the formula:

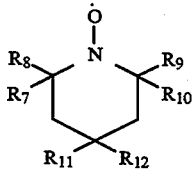

wherein each of $R_7$, $R_8$, $R_9$ and $R_{10}$ is an alkyl, aryl or substituted alkyl group having 1 to about 15 carbon atoms and no hydrogen is bound to the remaining valences on the carbon atoms bound to the nitrogen, and each of $R_{11}$ and $R_{12}$ is alkyl, hydrogen, aryl or a substituted heteroatom. As used herein, the term "alkyl" is meant to include cycloalkyl. The alkyl (or substituted) groups $R_7$-$R_{10}$ may be the same or different, and preferably contain 1 to 15 carbon atoms. Preferably, $R_7$-$R_{10}$ are methyl, ethyl, or propyl groups. In addition to hydrogen, the substituents may include, halogen, oxygen, nitrogen and the like. Typically, one of $R_{11}$ and $R_{12}$ is hydrogen, with the other one being a substituted heteroatom which does not interfere with the reaction. Suitable substituted heteroatoms include

—O—polymer and the like.

In a particularly preferred embodiment, the nitroxide is selected from the group consisting of 2,2,6,6-tetramethylpiperidine-1-oxyl, 4-methoxy-2,2,6,6-tetramethylpiperidine-1-oxyl, 4-ethoxy-2,2,6,6-tetramethylpiperidine-1-oxyl, 4-carbamoyl-2,2,6,6-tetramethyl-piperidine-1-oxyl, 4-acetylamino-2,2,6,6-tetramethylpiperidine-1-oxyl, 4-benzoylamino-2,2,6,6-tetramethylpiperidine-1-oxyl 4-pivaloylamido-2 2 6 6-tetramethylpiperidine-1oxyl, 4-decyloylamido-2,2,6,6-tetramethyl piperidine-1-oxyl, 4-dodecanoylamino-2,2,6,6-tetramethylpiperidine-1-oxyl, 4-octanoylamino-2,2,6,6-tetramethyl-piperidine-1-oxyl and mixtures thereof, with 2,2,6,6-tetramethylpiperidine-1-oxy),4-acetylamino-2,2,6,6-tetramethylpiperidine-1-oxyl, and 4-methoxy-2,2,6,6-tetramethylpiperidine-1-oxyl being especially preferred.

The $NO_x$-generating compound in the present process is typically selected from the group consisting of an alkali metal nitrosodisulfonate, nitric acid and mixtures thereof, with nitric acid being preferred. However, any compound which serves to generate $NO_x$ during the course of the reaction and which does not interfere with the reaction would be suitable. While not wishing to be bound by any particular theory, it is believed that nitrogen oxides ($NO_x$) are generated in the reaction and are the active species in the reaction.

The alkali metal nitrosodisulfonate suitable for use as a $NO_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added.

As used herein, the term "nitric acid" refers to nitric acid, fuming nitric acid or nitrous acid generated by contacting a nitrate or nitrite salt such as, for example, an alkali metal salt, a tetraalkylammonium salt, an alkaline earth salt or a rare earth salt, with a strong acid such as, for example, a mineral acid. The nitric acid suitable for use as a $NO_x$-generating compound in the present invention typically has a concentration in the range of from about 50 percent to about 100 percent, preferably about 70 percent. Generally, an amount of nitric acid in the range of from about 5 mole percent to about 200 mole percent, basis the moles of starting aryl methanol is utilized. The nitric acid is typically added to the reaction mixture after all of the other reactants have been added.

The reaction of the present invention can be carried out in the presence or absence of a solvent. A solvent is needed in the reaction when the reactants are not in liquid form at the reaction temperature. When the reaction is carried out in the presence of a solvent, the solvent is generally one in which the aryl methanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of heptane, acetonitrile, dichloromethane, glyme, tertiary amyl alcohol, carbon tetrachloride, chlorobenzene and mixtures thereof. In a preferred embodiment, the solvent is selected from dichloromethane, acetonitrile, glyme, heptane and mixtures thereof. The amount of solvent utilized in the process is typically in the range of from about 0.5:1 to about 100:1, preferably from about 2:1 to about 10:1, basis the weight of the starting aryl methanol.

The process of the present invention may be carried out in the presence or absence of an oxidant. In a preferred embodiment, the process is carried out in the presence of an oxidant. The oxidants suitable for use in the instant invention are those compounds which are capable, in the presence of a $NO_x$-generating compound, of oxidizing the stable free radical nitroxide to the oxoammonium salt. Suitable oxidants include oxygen-containing gases such as pure oxygen and oxygen in air. Whereas pure oxygen can be preferred to accomplish the desired conversion, the oxygen can also be diluted with an inert gas such as nitrogen, helium, argon, or other similar gas. For purposes of increasing the reaction rate, higher $O_2$ pressures such as, for example, up to about 2000 psig can be utilized. In a preferred embodiment, pure oxygen is used as the oxidant and it is bubbled into the reaction solution. In another embodiment, the reaction solution can be exposed or left open to the atmosphere.

The amounts and concentrations of the reactants utilized in the process of the instant invention can vary within wide ranges. The amount of stable free radical nitroxide is typically in the range of from about 0.1 mole percent to about 200 mole percent, preferably from about 5 mole percent to about 20 mole percent, basis the number of moles starting aryl methanol. Generally, the amount of $NO_x$-generating compound used is in the range of from about 5 mole percent to about 200 mole percent, basis the number of moles of aryl methanol.

The process of the present invention is typically conducted under mild conditions, with good results being obtained using a temperature in the range of from about 0° C. to about 100° C., preferably about 20° C. to about 70° C., and most preferably, about 35° C. to about 50° C. Reaction pressures are not critical although higher pressures can result in increased reaction rates. Pressures in the range of from about atmospheric pressure up to about 2000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.056 moles of aryl methanol, and 0.006 moles of the nitroxide, and solvent, if any, may be added to the reaction vessel, followed by the addition of 0.011 moles of 70 percent nitric acid and bubbling oxygen through the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such as high temperature water washing or distillation.

Depending upon process conditions and the nitroxide used, the selectivity to aldehyde obtained by this invention can be greater than about 99%. It should be understood that if the reaction of the present invention is allowed to continue after formation of the aldehydes, carboxylic acids rather than aldehydes may be produced. The products produced by the instant process can be used in a variety of detergent applications. For example, these products can be used as intermediates in the preparation of esters, imines, amines and acids.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

6 Grams of benzyl alcohol, 1.0 gram of 2,2,6,6-tetramethyl-piperidine-1-oxyl, 1 gram of 70 percent nitric acid and 25 milliliters of dichloromethane were charged to a 100 milliliter round bottomed flask. $O_2$ was bubbled through this mixture at a rate of 35 milliliters/minute at ambient pressure. The reaction temperature was held at 35° C. over a 2-hour period. The results are presented in Table I.

Example 2

6 Grams of benzyl alcohol, I gram of 2,2,6,6-tetramethyl-piperidine-1-oxyl, 1 gram of 70 percent nitric acid and 25 milliliters of dichloromethane were charged to a 100 milliliter round bottomed flask. This mixture was left open to the air at ambient pressure. The reaction was held at 35° C. over a 2hour period. The results are presented in Table I.

Example 3

6 Grams of benzyl alcohol, 1 gram of 2,2,6,6-tetramethyl-piperidine-1-oxyl, 1 gram of 70 percent nitric acid and 25 milliliters of dichloromethane were charged to a 100 milliliter round bottomed flask. The reaction was exposed to the atmosphere and held at 35° C. over a 5-hour period. This mixture was then left open to the air overnight. The results are presented in Table I.

Example 4

6 Grams of benzyl alcohol, 1 gram of 2,2,6,6-tetramethyl-piperidine-1-oxyl and 2 grams of 70 percent nitric acid were charged to a 100 milliliter round bottomed flask. Air was exposed to this mixture at ambient pressure. The reaction temperature was held at 35° C. over a 2-hour period. The results are presented in Table I.

Comparative Example A

Comparative Example A was carried out in a manner similar to Example 1 except that no nitroxide was used. The results are presented in Table I.

Comparative Example B

Comparative Example B was carried out in a manner similar to Example 1 except that no nitric acid was used. The results are presented in Table I.

As can be seen in Table I, nitroxide and nitric acid are necessary for the oxidation of the aryl methanol to proceed.

TABLE I

Oxidation of Aryl Methanols to Aldehydes

| | % Conversion | % Sel. Aldehydes |
|---|---|---|
| Example 1 | 41 | >99 |
| Example 2 | 28 | >99 |
| Example 3 | 60 | >99 |
| Example 4 | 78 | 92 |
| Comparative Example A | <1 | 0 |
| Comparative Example B | 0 | 0 |

What is claimed is:

1. A process for the preparation of an aldehyde which comprises reacting the corresponding aryl methanol with a stable free radical nitroxide having the formula:

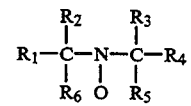

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$–$R_6$ are not all alkyl groups, or a substituted alkyl group having 1 to about 15 carbon atoms wherein the substituent is hydrogen, cyano, —$CONH_2$, —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains at least 3 carbon atoms and up to two heteroatoms of O or N, (2) the

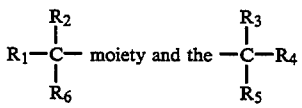

moiety individually are aryl, or (3) the

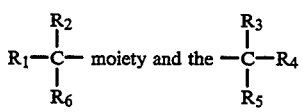

moiety together form a bicyclic ring with the proviso that the group directly adjacent to the N—O is a bridgehead C—H, or a fully alkylated carbon, in the presence of a NO$_x$-generating compound, at, a temperature in the range of from about 0° C. to about 100° C. and thereafter separating out the aldehyde.

2. The process of claim 1 wherein said aryl methanol has a carbon number in the range from about 5 to about 50.

3. The process of claim 2 wherein said aryl methanol has a carbon number in the range from about, 6 to about 30.

4. The process of claim 3 wherein the aryl methanol is selected from the group consisting of benzyl alcohol, 4-nitrobenzyl alcohol, 3-chlorobenzyl alcohol, 4-methylbenzyl alcohol, 4-chlorobenzyl alcohol, 3-methylbenzyl alcohol, 3-ethylbenzyl alcohol, 3-methoxybenzyl alcohol and mixtures thereof.

5. The process of claim 4 wherein the aryl methanol is benzyl alcohol.

6. The process of claim I wherein the stable free radical nitroxide is selected from the group consisting of 2,2,6,6,-tetramethylpiperidine-1-oxyl, 2,2,5,5-tetramethylpyrrolidin-1-oxyl,2,2,7,7-tetramethylcycloheptan-1-oxyl, and mixtures thereof.

7. The process of claim I wherein the stable free radical nitroxide has the formula:

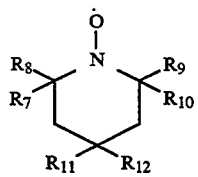

wherein each of R$_7$, R$_8$, R$_9$ and R$_{10}$ is an alkyl, aryl or heteroatom substituted alkyl group having 1 to about 15 carbon atoms and each of R$_{11}$ and R$_{12}$ is alkyl, hydrogen, aryl or a substituted heteroatom.

8. The process of claim 7 wherein the stable free radical nitroxide is selected from the group consisting of 2,2,6,6-tetramethylpiperidine-1-oxyl, 4-methoxy-2,2,6,6-tetramethylpiperidine-1-oxyl, 4-ethoxy-2,2,6,6-tetramethylpiperidine-1-oxyl, 4-acetylamino-2,2,6,6-tetramethyl-piperidine-1oxyl, 4-carbamoyl-2,2,6,6-tetramethylpiperidine-1-oxyl, 4-benzoylamino2,2,6,6-tetra-methylpiperidine-1-oxyl, 4-pivaloylamido-2,2,6,6-tetramethylpiperidine-1-oxyl, 4-decyloylamido-2,2,6,6-tetramethylpiperidine-1-oxyl, 4-dodecanoylamino-2,2,6,6-tetramethylpiperidine-1-oxyl,4-octanoylamino-2,2,6,6-tetramethylpiperidine-1-oxyl and mixtures thereof.

9. The process of claim 8 wherein the stable free radical nitroxide is selected from the group consisting of 2,2,6,6-tetramethylpiperidine-1-oxyl, 4-acetylamino-2,2,6,6-tetramethylpiperidine-1-oxyl, 4-methoxy-2,2,6,6-tetramethyl-piperidine-1-oxyl and mixtures thereof.

10. The process of claim 1 wherein said process is carried out in the presence of a solvent.

11. The process of claim 10 wherein said process the solvent is selected from the group consisting of heptane, acetonitrile, dichloromethane, glyme, tertiary amyl alcohol, carbon tetrachloride, chlorobenzene and mixtures thereof.

12. The process of claim 1 wherein said NO$_x$-generating compound is selected from the group consisting of nitric acid, an alkali metal nitrosodisulfonate and mixtures thereof.

13. The process of claim 12 wherein said NO$_x$-generating compound is nitric acid.

14. The process of claim 13 wherein said nitric acid is selected from the group consisting of fuming nitric acid, nitrous acid generated by contacting an alkali metal nitrite with mineral acid, nitric acid generated by contacting an alkali metal nitrate with mineral acid, and mixtures thereof.

15. The process of claim 13 wherein the amount of nitric acid is in the range of from about 5 mole percent to about 200 mole percent, basis the moles of starting aryl methanol.

16. The process of claim 12 wherein said NO$_x$-generating compound is an alkali metal nitrosodisulfonate.

17. The process of claim 16 wherein the amount of alkali metal nitrosodisulfonate is in the range of from about 5 mole percent to about 200 mole percent, basis the moles of starting aryl methanol.

18. The process of claim 16 wherein said alkali metal nitrosodisulfonate is potassium nitrosodisulfonate.

19. The process of claim 1 wherein said aryl methanol is contacted with said stable free radical nitroxide, followed by the addition thereto of said NO$_x$-generating compound.

20. The process of claim 19 wherein the amount of stable free radical nitroxide is in the range of from about 0.1 mole percent to about 200 mole percent, basis the number of moles of aryl methanol.

21. The process of claim 19 wherein the amount of NO$_x$-generating compound is in the range of from about 5 mole percent to about 200 mole percent, basis the number of moles of aryl methanol.

22. The process of claim 1 wherein said process is carried out in the presence of an oxidant.

23. The process of claim 22 wherein said oxidant is an oxygen-containing gas.

24. The process of claim 23 wherein said oxygen-containing gas is selected from the group consisting of pure oxygen and air.

25. The process of claim I wherein said process is carried out at a temperature in the range of from about 20° C. to about 70° C. and at atmospheric pressure.

* * * * *